(12) United States Patent
Ibrahim et al.

(10) Patent No.: US 11,141,101 B2
(45) Date of Patent: *Oct. 12, 2021

(54) TOPICAL PRODUCT DISPENSING TOOL

(71) Applicant: SKIN DEPTH INC., Oakville (CA)

(72) Inventors: Noelle Ibrahim, Oakville (CA); Takis Zourntos, Oakville (CA); Ivana Knezevic, Toronto (CA); Jerry Tan, Windsor (CA)

(73) Assignee: SKIN DEPTH INC., Oakville (CA)

( * ) Notice: Subject to any disclaimer, the term of this patent is extended or adjusted under 35 U.S.C. 154(b) by 302 days.

This patent is subject to a terminal disclaimer.

(21) Appl. No.: 16/263,948

(22) Filed: Jan. 31, 2019

(65) Prior Publication Data

US 2019/0159718 A1 May 30, 2019

Related U.S. Application Data

(63) Continuation of application No. 14/967,034, filed on Dec. 11, 2015, now Pat. No. 10,219,737.

(Continued)

(51) Int. Cl.
*A61B 5/00* (2006.01)

(52) U.S. Cl.
CPC .................. *A61B 5/445* (2013.01)

(58) Field of Classification Search
CPC .......... A61B 5/445; A61M 2205/3317; A61M 2205/3379; A61M 35/003
See application file for complete search history.

(56) References Cited

U.S. PATENT DOCUMENTS 6,251,070 B1  6/2001  Khazaka
6,516,245 B1  2/2003  Dirksing et al.
(Continued)

FOREIGN PATENT DOCUMENTS

CA  2036659 A1  8/1991
CA  2168558 C   3/1995
(Continued)

OTHER PUBLICATIONS

Oxford Dictionary on Lexico.com definition of irritation, www.lexico.com/en/definition/irritation, Retrieved Feb. 24, 2021.*

(Continued)

*Primary Examiner* — Tatyana Zalukaeva
*Assistant Examiner* — Jessica R Arble
(74) *Attorney, Agent, or Firm* — Dickinson Wright PLLC

(57) ABSTRACT

A computer-implemented method can include receiving a first image input from a user, determining values of biological properties of the user, determining a first formulation, controlling a plurality of servomotors, receiving a second image input from a user, determining a second value of one of the biological properties of the user, comparing the first and second values, changing another of the values, determining a second formulation, and again controlling the plurality of servomotors. The image inputs can include images of the users skin. The values can be representative of a sensitivity of the user's skin to one or more materials and a current level of irritation of the user's skin. The formulations can contain a plurality of materials and can be configured to inhibit irritation of the user's skin based on the values of the biological properties of the skin.

37 Claims, 4 Drawing Sheets

Related U.S. Application Data

(60) Provisional application No. 62/090,733, filed on Dec. 11, 2014.

(56) References Cited

U.S. PATENT DOCUMENTS

| | | | |
|---|---|---|---|
| 7,349,857 | B2 | 3/2008 | Manzo |
| 8,593,834 | B2 | 11/2013 | Igarashi |
| 9,119,918 | B2 | 9/2015 | Robertson et al. |
| 9,122,919 | B2 | 9/2015 | Howell |
| 10,219,737 | B2 * | 3/2019 | Ibrahim ................. A61B 5/445 |
| 2006/0010004 | A1 | 1/2006 | Deckner |
| 2007/0035815 | A1 * | 2/2007 | Edgar ........................ B41J 3/36 |
| | | | 359/359 |
| 2010/0228106 | A1 | 9/2010 | Khazaka |
| 2010/0233111 | A1 | 9/2010 | Wang et al. |
| 2011/0288680 | A1 * | 11/2011 | Samain ............... B01F 13/1055 |
| | | | 700/239 |
| 2014/0267664 | A1 | 9/2014 | Gross et al. |
| 2015/0230863 | A1 * | 8/2015 | Youngquist .......... A61B 5/4833 |
| | | | 606/9 |
| 2017/0256084 | A1 * | 9/2017 | Iglehart ............... G06F 3/04845 |

FOREIGN PATENT DOCUMENTS

| | | | |
|---|---|---|---|
| EP | 1429640 | B1 | 3/2003 |
| EP | 1737339 | B1 | 1/2009 |
| WO | 1998030189 | A2 | 7/1998 |
| WO | 2001091600 | A2 | 12/2001 |
| WO | 2004091477 | A2 | 10/2004 |
| WO | 2011067707 | A2 | 6/2011 |
| WO | 2013159101 | A2 | 10/2013 |
| WO | 2014047712 | A1 | 4/2014 |
| WO | 2014095204 | A2 | 6/2014 |
| WO | WO2015017798 | A3 | 2/2015 |

OTHER PUBLICATIONS

Weil, "Romy Paris: A 'Next-Generation' Beauty Concept", 2015 (http://wwd.com/beauty-industry-news/skin-care/romy-paris-a-next-generation-beauty-concept-10238267).

O'Doherty, et al., "Sub-epiderimal imaging using polarized light spectroscopy for assessment of skin microcirculation", Skin Research and Technology, 2007, 13: 472-484.

Rosenbaum, "Casio Pharmacokinetics and Pharmacodynamics: An integrated Textbook and Computer Simulations", Chapter 17.6 Tolerance Models, John Wiley & Sons, Inc., 2011, Hoboken, NJ, pp. 344-345.

Caruso, Antonello L. G.: Personalized drug dosing through modeling and feedback; PHD Disseration: 2009; All pages are presumed relevant; Zurich, Switzerland.

Sachs, Dana L. and Voorhees, John J.; Cosmeceuticals and Cosmetic Practice: Book; Published 2014; Chapter 8: Vitamin A—Retiniods and the Treatment of Aging Skin; John Wiley & Sons, Ltd.; International Publication.

Murthy, S. Narasimha; Dermetokinetics of Therapeutic Agents: Book; Apr. 15, 2011, pp. 44-61; CRC Press.

Patwardhan, Sachin V., Kaczvinsky, Joseph R., Joa, James F., Canfield, Douglas; Auto-Classification of Acne Lesions Using Multimodal Imaging; Journal of Drugs in Dermatology; Jul. 2013: All pages are presumed relevant; vol. 12, Issue 7.

* cited by examiner

TOPICAL PRODUCT DISPENSING TOOL

CROSS-REFERENCE TO RELATED APPLICATIONS

This application is a continuation of U.S. patent application Ser. No. 14/967,034, filed Dec. 11, 2015, which claims the benefit of U.S. Provisional Patent Application Ser. No. 62/090,733, filed on 11 Dec. 2014, which are each hereby incorporated by reference in its entirety.

BACKGROUND

1. Field

The present disclosure relates to relates to an apparatus and method for formulating a customized personal care composition for a particular individual.

2. Description of Related Prior Art

U.S. Pat. No. 7,349,857 discloses a process for formulating a customized skin care product. The process involves determining an individual skin structure and function at a point in time for the purpose of determining and formulating skin care products that remedy the deficiencies observed in the skin. Objective and repeatable dermal biometric instrumentation techniques can be used to measure skin moisture content, sebum content, firmness and elasticity properties, skin thickness, transepidermal water loss, skin pH and to perform a photo analysis of the face with UV and visible light. By customizing the skin care products, the individually added active ingredients can be controlled, the diluents can be modified, dermal penetration rates can be controlled, the surfactant systems can be adjusted, and the stability of the product can be controlled. To prevent the loss of active materials in the product, the skin care product is manufactured for an individual consumer and is only sold in a quantity of a three months supply. Additionally, a variety of ingredients can be combined that a mass produced product cannot contain due to stability/compatibility issues.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A computer-implemented method can include receiving, at a computing device having one or more processors, a first image input from a user, the first image input including a first image of a portion of the user's skin; determining, at the computing device, a first value of a first biological property of the user's skin and a first value of a second biological property of the user's skin, both first values based at least in part on the first image input, the first biological property representative of a sensitivity of the user's skin to one or more materials, the second biological property representative of a response of the user's skin to one or more materials; determining, at the computing device, a first formulation containing a plurality of materials, the first formulation based on the first value of the first biological property of the user's skin; receiving, at the computing device, a second image input from the user, the second image input including a second image of the portion of the user's skin after application of the first formulation containing the first quantities of materials; determining, at the computing device, a second value of the second biological property of the user's skin based at least in part on the second image input; comparing, at the computing device, respectively, the first value of the second biological property and the second value of the second biological property; updating, at the computing device, the first value of the first biological property of the user's skin to a second value of the first biological property of the user's skin based on said comparing; and determining, at the computing device, a second formulation containing the plurality of materials based at least in part on the second value of the first biological property of the user's skin.

A computing device can comprise one or more processors; and a non-transitory, computer readable medium storing instructions that, when executed by the one or more processors, cause the computing device to perform operations. The operations can comprise: receiving a first image input from a user, the first image input including a first image of a portion of the user's skin; determining a first value of a first biological property of the user's skin and a first value of a second biological property of the user's skin, both first values based at least in part on the first image input, the first value representative of a sensitivity of the user's skin to one or more materials, the second value representative of a response of the user's skin; determining a first formulation containing a plurality of materials, the first formulation based on the first value of the first biological property of the user's skin; receiving after said controlling, a second image input from the user, the second image input including a second image of the portion of the user's skin after application of the first formulation containing the first quantities of material; determining a second value of the second biological property of the user's skin based at least in part on the second image input; comparing respectively, the first value of the second biological property and the second value of the second biological property; updating the first value of the first biological property of the user's skin to a second value of the first biological property of the user's skin based on said comparing; and determining a second formulation containing the plurality of materials based at least in part on the second value of the first biological property of the user's skin.

BRIEF DESCRIPTION OF THE DRAWINGS

The detailed description set forth below references the following drawings.

DETAILED DESCRIPTION

Figure 1:
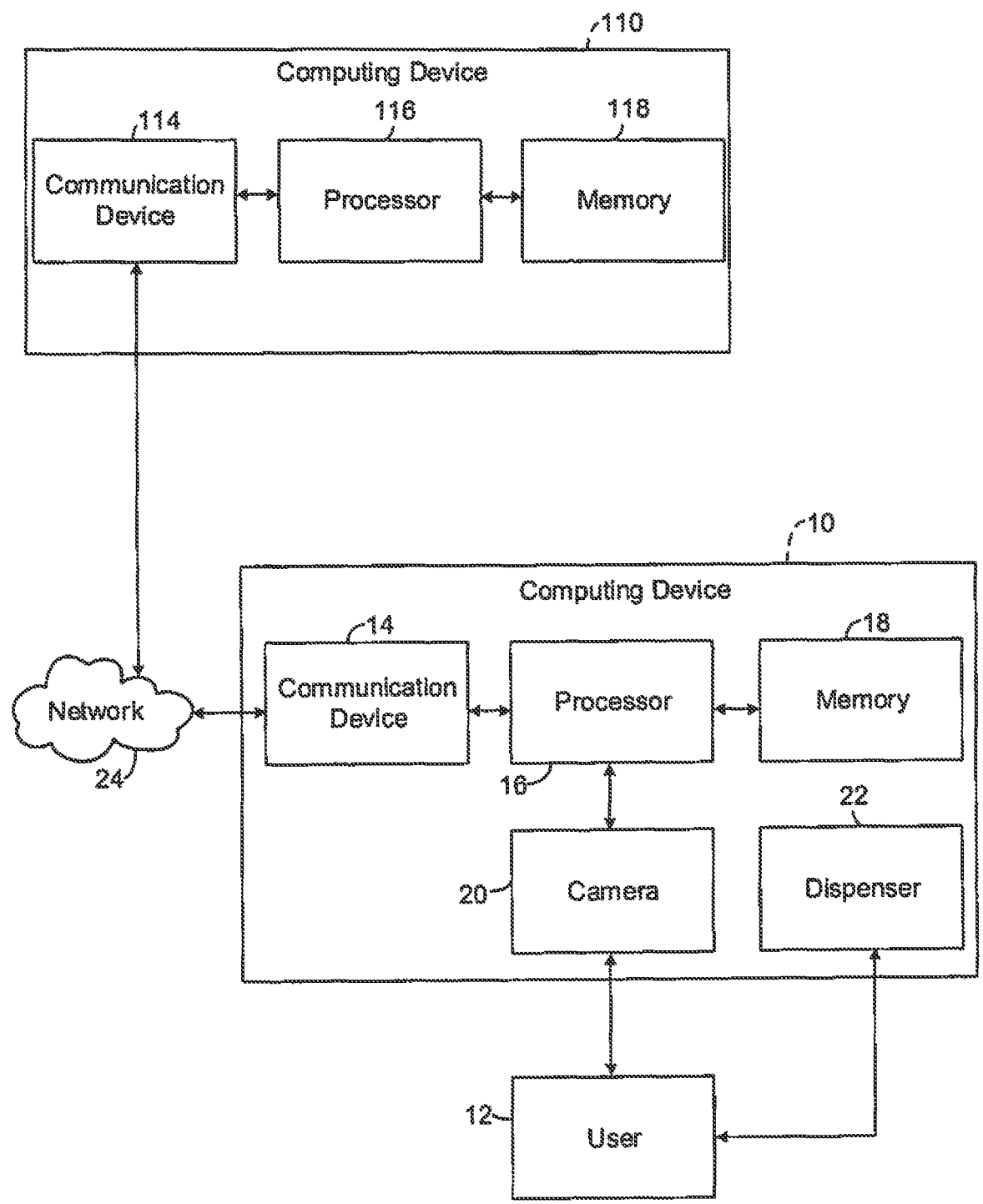
FIG. 1 is a functional block diagram of an exemplary computing device according to some implementations of the present disclosure.

The present disclosure, as demonstrated by the exemplary embodiment described below, can provide a personal care product formulator with a sensor or a sensor array and feedback analysis that measures and adjusts the dose and composition of cosmeceutical or other agents in response to the user reaction.

Personal care products can include skin care products, by way of example and not limitation. One or more embodiments of the present disclosure will apply one or more sensors to detect biological features of a user and determine a formulation (cosmeceutical or other) that is personalized to that user's needs based on the sensed biological features as well as any user input data. Exemplary biological features can be acne legion count, tissue inflammation, skin dryness, presence of bacteria, extent and severity of sun damage or actinic keratosis, and/or skin oil level. The user input data can be data acquired through typing, voice, and/or uploading to a server.

The personalized formula will be mixed in a mixer operably communicating with the at least one sensor in one or more embodiments of the present disclosure. One or more embodiments of the present disclosure can include analytical software and can be configured for home use, rather than at the point of sale.

One or more embodiments of the present disclosure can include computer software containing a learning and updating algorithm based on Machine learning or related algorithms that will learn the user's response to different applied products and adjust the formulations of future delivered products based on a desired response to the product on a daily basis. Embodiments can sense and quantify values of the initial state of the user's skin, hair or other measured target of the personal care product prior to the application of the product as well as responses after the application of a known formulation. Measurements can be taken on a daily basis, rather than just once and product changes can occur daily or as needed to adjust to skin oiliness, etc., and the individual response.

Data measured with a device according to one or more embodiments of the present disclosure can be communicated to a central database along with meta-data entered by the user. Such data can include subjective impressions of product efficacy for the purposes of conducting medical research using both labeled and unlabeled data and deep learning algorithms. This database can be used subsequently in the product formulation process, by establishing a cohort of users with similar features and projected dose response or side effect curves.

Data gathering can be designed to be as controlled in the device for determining the formulation and the mixer. For example, data can be collected with only known variables changes and without any uncontrolled extraneous variable changes that could obfuscate the relationship between dependent variables (outcomes) and independent variables (causal factors) for any given response measurement. Any uncontrolled variable changes should be considered and accounted for when interpreting the meaning of measurements of a user or a user response to any given therapy in before and after measurements or in comparison to control groups. For example, background noise must be filtered out and placement of the sensor on the body must be accounted for as measurements of skin on the arm, for example, cannot be directly compared to skin on the face.

One or more embodiments of the present disclosure can include wearable or handheld sensors, such as electrodermal or multi-photon optical sensors that may be placed in contact with a patch of skin. Such sensors may be used and data can be communicated wirelessly to the mixer and controller that will mix formulations of personal care products.

No feedback device is currently on the market to personalize a product after the user has tried it, taking into account the skin's reaction to the treatment plan. Additionally, many users of cosmeceutical products find that they must regularly alter their plan depending on the phase of their menstrual cycle, foods eaten, sleep and other unaccounted for influencing factors. No study regarding treatment plans that vary components of a skin care regime on a day to day basis exists. Finally, no product exists on the market that allows users to empirically "see for themselves," by using scientific measurements and allowing the user to track records of physical and psychological response to the treatment plan, the results of the application of a skin care regime, away from the point of sale. This would be desirable to many users as a large element of distrust of the efficacy of cosmeceutical agents exits, due to the lack of regulation and heavy marketing involved.

The response algorithm and concept may be applied to personal care products not related to skin, such as the saliva and various agents in toothpaste, including whitening agents, which, when properly applied can fight and prevent periodontal disease in the early stages. Hair care products, eye drops, deodorant and other products may also be personalized using one or more embodiments of the present disclosure.

FIG. 1 is a functional block diagram of an exemplary computing device according to some implementations of the present disclosure. Implementations of the present disclosure can include a computing device, such as an exemplary computing device 10. The computing device 10 can be operated by a user 12. While a single computing device 10 and its associated user 12 and example components are described and referred to hereinafter, it should be appreciated that a computing device according to one or more implementations of the present disclosure can be cooperatively defined by structures that are physically remote from one another, such, for example, a server and smartphone. Examples of the computing device 10 include desktop computers, laptop computers, tablet computers, and mobile phones. In some embodiments, the computing device 10 can be a mobile computing device associated with the user 12. In some embodiments, the computing device 10 can be a server, wherein input from the user 12 is received by the computing device 10 from another computing device associated with the user 12.

The computing device 10 can include a communication device 14, a processor 16, and a memory 18. The computing device 10 can also include a camera 20 and a dispenser 22. By way of example and not limitation, in one or more implementations of the present disclosure, the camera 20 can be a Point Grey Blackfly BFLY-U3-23S6C-C Machine Vision Camera with appropriate lensing, or possibly a pair of such cameras arranged for stereovision suitable for mapping the topography of the face in order to determine the severity of lesions, sun damage, wrinkles and creases. In other implementations of the present disclosure, a computing device can include other peripherals, such as a display (touch screen or otherwise), a mouse, a keyboard, and/or a microphone.

The communication device 14 is configured for communication between the processor 16 and other devices, e.g., a user's computing device, via a network 24. The network 24 can include a local area network (LAN), a wide area network (WAN), e.g., the Internet, or a combination thereof. The communication device 14 can include any suitable communication components, such as a transceiver. Specifically, the communication device 14 can transmit requests for data to other computing devices (such as exemplary server computing device 110) from the processor 16. The communication device 14 can transmit data and requests to process the data to the computing device 110 from the processor 16. The communication device 14 can provide response(s) to these requests to the processor 16. The communication device 14 can also provide system updates to the processor 16.

The memory 18 can be configured to store information at the computing device 10, such as skin conditions and topical product formulations correlated with respect to one another. The skin conditions stored in memory 18 can include a data associated with the visual attributes of such skin conditions so that images captured by the camera 20 can be correlated to one or more of the skin conditions by the processor 16. The skin conditions stored in memory 18 can include a data associated with the compatibility of various materials held by the dispenser 22 so that the materials dispensed by the dispenser 22 do not cause or exacerbate irritation of the skin of the user 12. Further, the skin conditions stored in memory 18 can include a data associated with the compatibility of various materials held by the dispenser 22 so that the materials dispensed by the dispenser 22 heal irritation and/or promote the health of the skin of the user 12. The skin conditions stored in memory 18 can include formulations or algorithms for deriving formulations for topical products.

Attributes of the user 12 can be stored in memory 18. For example, a "ghost" photo image can be stored in order to align future images to enhance consistency of the analysis. The skin tone and hue of the skin can be retained in memory 18. Various parameters that a physician may find relevant can be retained in memory 18, such as parameters that tend to limit a range of materials and material quantities that can be utilized safely by the user 12. Genetic information from the user 12 can also be stored in memory 18.

Memory 18 can be defined in various ways in implementations of the present disclosure. Memory 18 can be any suitable storage medium (flash, hard disk, etc.). Memory 18 can be non-transitory in nature, and may include volatile and non-volatile, and removable and non-removable media implemented in any method or technology for storage of information, such as computer-readable instructions, data structures, program modules or other data. Memory 18 can further include RAM, ROM, erasable programmable read-only memory (EPROM), electrically erasable programmable read-only memory (EEPROM), flash memory or other solid state memory technology, CD-ROM, digital versatile disks (DVD), or other optical storage, magnetic cassettes, magnetic tape, magnetic disk storage or other magnetic storage devices, or any other medium that can be used to store the desired information and which can be accessed by the controller 16. Memory 18 can store computer readable instructions, data structures or other program modules. By way of example, and not limitation, communication media may include wired media such as a wired network or direct-wired connection, and wireless media such as acoustic, RF, infrared and other wireless media. Combinations of any of the above may also be included within the scope of computer readable media.

The processor 16 can be configured to control operation of the computing device 10. It should be appreciated that the term "processor" as used herein can refer to both a single processor and two or more processors operating in a parallel or distributed architecture. The processor 16 can operate under the control of an operating system, kernel and/or firmware and can execute or otherwise rely upon various computer software applications, components, programs, objects, modules, data structures, etc. Moreover, various applications, components, programs, objects, modules, etc. may also execute on one or more processors in another computing device coupled to processor 16, e.g., in a distributed or client-server computing environment, whereby the processing required to implement the functions of embodiments of the present disclosure may be allocated to multiple computers over the network 34. The processor 16 can be configured to perform general functions including, but not limited to, loading/executing an operating system of the computing device 10, controlling communication via the communication device 14, and controlling read/write operations at the memory 18. The processor 18 can also be configured to perform specific functions relating to at least a portion of the present disclosure including, but not limited to, loading/executing a topical product dispensing tool application and one or more other applications at the computing device 10. By way of example and not limitation, in one or more implementations of the present disclosure, the processor 16 can be a multi-processor unit consisting of one or more Nvidia Tesla K80 GPU accelerators used in concert with a main computing motherboard based on one or more Intel XEON Processor E7 v3 chips.

Figure 2:
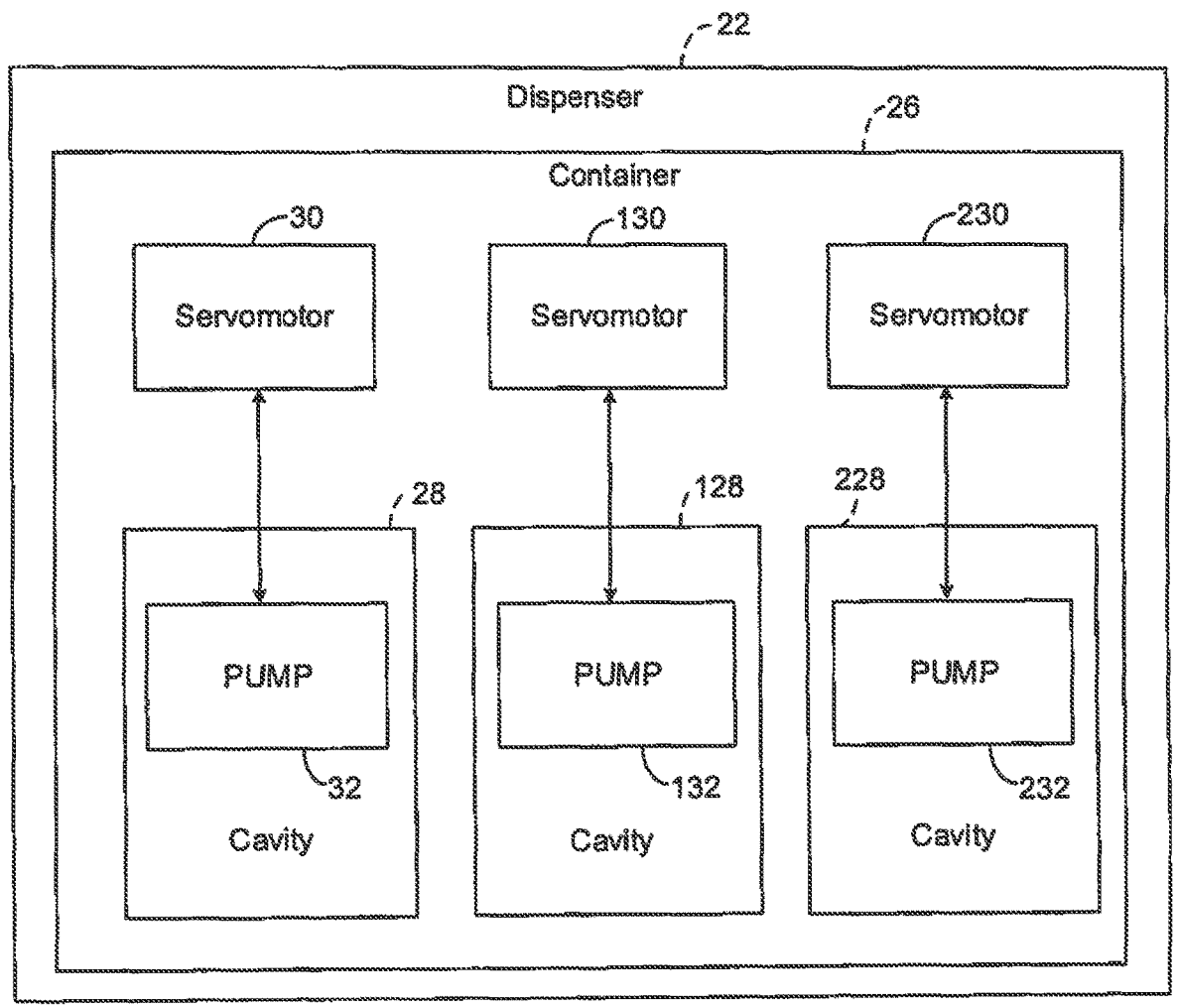
FIG. 2 is a functional block diagram of an exemplary dispenser according to some implementations of the present disclosure.

FIG. 2 is a functional block diagram of an exemplary dispenser 22 according to some implementations of the present disclosure. The dispenser 22 can include a container 26 having a plurality of cavities 28, 128, 228. Each of the cavities 28, 128, 228 can contain a respective material of formulations for application on the skin of the user 12. The dispenser 22 can also include a plurality of servomotors 30, 130, 230 and a plurality of pumps 32, 132, 232. Each of the plurality of servomotors 30, 130, 230 can be individually engaged with one of the pumps 32, 132, 232. For example, when the servomotor 30 is activated by the processor 16, the servomotor 30 energizes and causes the pump 32 to urge material out of the cavity 28. The user 12 can mix the quantities of material dispensed by the dispenser 22 to produce the formulation and can apply the formulation to his/her skin. By way of example and not limitation, the following materials can be stored in one of the cavities 28, 128, 228 in one or more implementations of the present disclosure: the three components A, B and C can be A oil/water emulsion (the vehicle), B can be a retinol microsponge formulation with a given concentration and C can be a 15% L-ascorbic acid (vitamin C) formulation.

By way of example and not limitation, in one or more implementations of the present disclosure, the dispenser 22 can be an arrangement of syringe pumps, such as the Warner Instruments Syringe Pump 11 Elite or the AITECS 21S PLUS dual syringe pump or variations, or a single syringe pump in combination with a carousel or linear array of syringe cartridges which are aligned with the syringe pump through a positioning system (using, for example, a position-servo system like the Micromo 2232S024BX4SAES-4096+22F 4:1, using magnetic absolute position encoder and brushless dc motor with planetary gearhead in closed-loop operation). In this case a single linear positioning system can be implemented around a linear position servo, such as the Micromo 2237S036CXR3965+BS22-1.5+HEDS5540106+BSA01+OPEC04, utilizing a brushless DC motor with integrated ball screw and position feedback.

Figure 3:
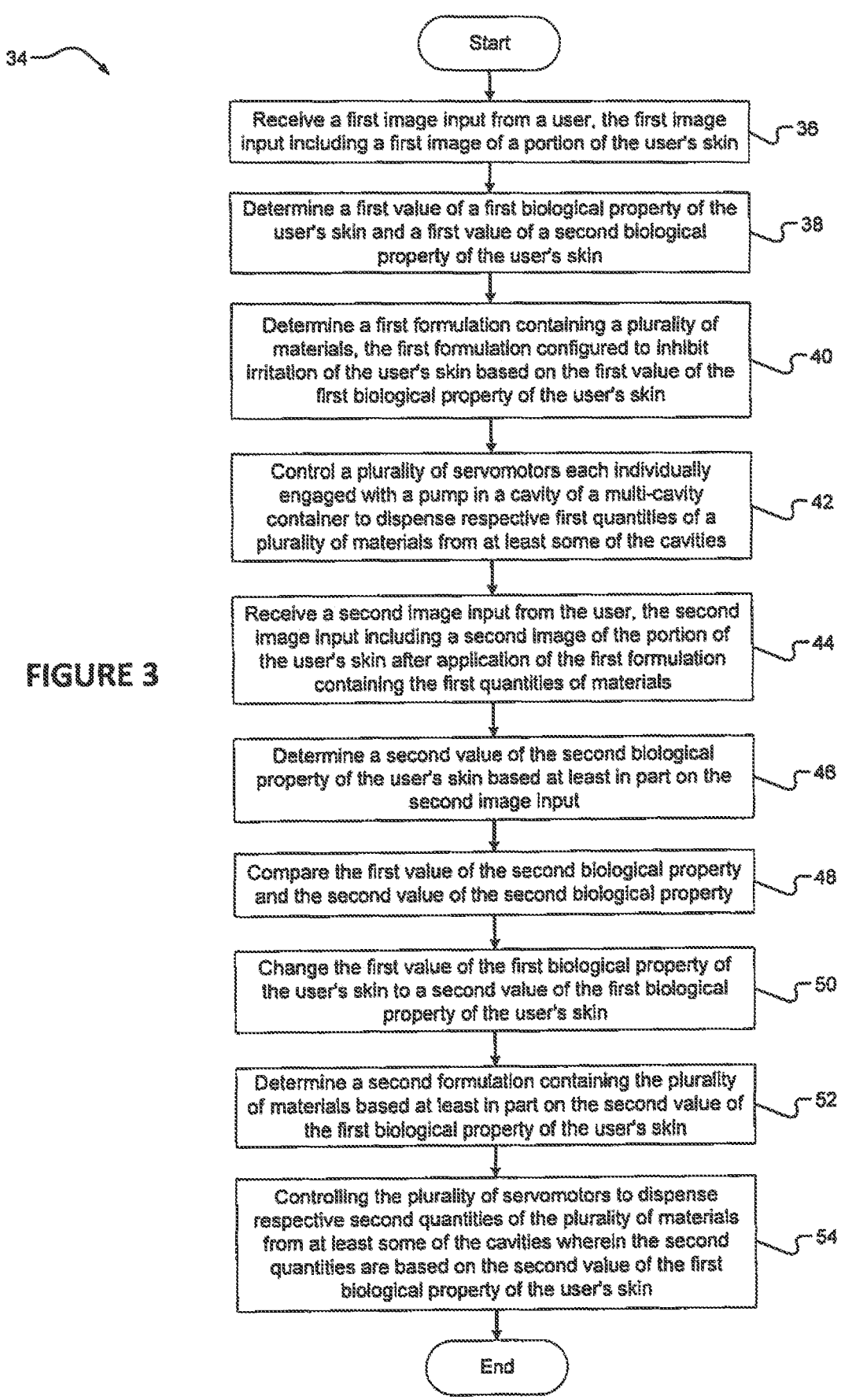
FIG. 3 is a flow diagram of an example method according to some implementations of the present disclosure.

FIG. 3 is a flow diagram of an example method 34 according to some implementations of the present disclosure. At 36, the computing device 10 can receive a first image input from the user 12. The first image input including a first image of a portion of the skin of the user 12. The user 12 can capture the image with the camera 20. The image can be an infrared or ultraviolet image in one or more implementations of the present disclosure. The user 12 can be a subject in a research study, a patient of a dermatologist or family physician, or a consumer at home or in a mercantile. The user 12 can be a consumer desiring a sunscreen with a particular tint for a particular range of skin tones. The user 12 can be a consumer desiring anti-aging products and in preventing sun damage, possibly by detecting subtle changes in skin tone (and having their sunscreen tuned accordingly), ensuring the proper treatment of actinic keratosis (AK) (tuning their medicine accordingly, while managing side effects). The user 12 can be a subject of a cosmetic company study.

At 38, the computing device 10 can determine a first value of a first biological property of the skin of the user 12 and a first value of a second biological property of the skin of the user 12. Both first values can be based at least in part on the first image input. The first biological property can be representative of a sensitivity of the skin of the user 12 to one or more materials in the dispenser 22. The second biological property can be representative of a current level of irritation of the skin of the user 12.

By way of example and not limitation, in one or more implementations of the present disclosure, the processor 16 can apply Media Cybernetics Image-Pro Premier 3D to analyze the first image input and determine the first values. For example, processor 16, executing the Image-Pro software, can identify, classify and count lesions. Lesions can be classified as comedones (open and closed), papules, pustules, nodules or cysts and localization. Features in the image can be identified as primary and secondary lesions (scars). Holistic methods can be applied by the processor 16, such as convolutional neural networks, semi-quantitative assessments of extent of acne using classification methods or possibly techniques from natural language processing.

At 40, the computing device 10 can determine a first formulation containing a plurality of materials. The first formulation can be configured to inhibit irritation of the user's skin based on the first value of the first biological property of the user's skin. The first formulation can also be configured to heal irritation of the user's skin based on the first value of the second biological property of the user's skin.

It is noted that the first values of the first and second biological properties and/or the first formulation can be determined based on reference to data supplemental to the image data. One or more implementations of the present disclosure can utilize meta-data or demographic data provided by the user 12 through an appropriate user interface to determine the first and second biological properties and/or the first formulation. One or more implementations of the present disclosure can utilize previously-stored user satisfaction data as well as doctor-generated data. Such data can be stored in memory 18, or memory 118 of computing device 110. Doctor-generated data can include doctor preferences or user-adjusted severity ratings. Such data could act as an over-ride to a formulation derived initially by the processor 16. The image can be compared with other images stored in memory 18 or memory 118. Machine learning algorithms can be applied based on latent variables in memory 18 or memory 118. The processor 16, through the communication device 14, can communicate with the processor 116, through the communication device 114, to extract data from memory 118. Alternatively, the processor 16 can communicate a derived formulation to the processor 116, the processor 116 can assess the formulation in view of data stored in memory 118, and the processor 116 can communicate affirmation of the formulation or recommend a revised formulation. One or more implementations of the present disclosure can store formulations associated with a particular user and/or a particular skin sample in memory 18 or memory 118.

One or more implementations of the present disclosure can utilize pre-authorized formulations by a physician. For example, a proposed, first formulation can be directed to a physician for approval. If the physician does not approve the proposed, first formulation, the computing device 10 can generate an alternative formulation for consideration by the physician.

At 42, the computing device 10, through the processor 16, can control the plurality of servomotors 30, 130, 230 as necessary to dispense respective first quantities of a plurality of materials from at least some of the cavities 28, 128, 228 with the pumps 32, 132, 232. Each cavity can contain a respective material of the first formulation for application on the skin of the user 12.

The dispenser 22 could make use of automatic pumps and/or automatic mixing (automatic pumps with manual mixing may be best compromise) in various implementations of the present disclosure. The container 26 can contain active ingredients, moisturizers, tints, and scents. In one or more implementations of the present disclosure, the dispenser 22 could be physically remote from other components of the computing device 10. For example, a dispenser could be positionable in an environment such as a bath tub or shower and communicate wirelessly with the processor 16.

Embodiments of the present disclosure can be applicable to a wide range of material dosing scenarios, including both prescription and non-prescription drugs. Furthermore, as data is collected and knowledge and understanding of the relationships between quantities described in mathematical relationships described herewithin are better understood by embodiments of the present disclosure, changes to the mathematical descriptions of the relationships between measured quantities and dosing outcomes may be made to reflect the acquired data. This data and feedback is a part of the desirability of embodiments of the present disclosure.

In one example, the three components A, B and C are A=oil/water emulsion (the vehicle), B is a retinol microsponge formulation with a given concentration and C is a 15% L-ascorbic acid (vitamin C) formulation. It is noted that this example is for illustration purposes and that other components can be utilized in one or more embodiments of the present disclosure. One or more embodiments of the present disclosure can determine user-specific formulations that may be changed according to user response. For most cases, the following measurements can be made in the current example, although it should be understood that as techniques develop and become practical more measurements may be added to the measured "response". There are at least two categories of measurements: toxic response and therapeutic response.

"Toxic response" can be viewed as at least partially defining the second biological value during initial use of the embodiment and subsequent uses. Toxic response (hereafter T1, T2, T3, T4) can be measured as follows. T1 can be a measure of Erythema made using cross polarization spectroscopy wherein white LEDs and camera lenses can be used with polarization filters oriented at ninety degrees. A material such as, for example, the ThorLabs LPVISE2X2 triacetate, can be cut to the appropriate shape and dimensions for this purpose. The difference between the intensities of the red channel and green channels in each pixel will be made over a photograph of the patch of skin taken using cross polarization spectroscopy. The total magnitude of the difference in intensity of the blue channel and green channel will be representative of the amount of erythema (redness from inflammation) present in the skin. T1 can equal:

$$\Sigma_{pixels}(\text{red channel intensity value} - \text{green channel intensity value})$$

The equation above is one example of a quantitative measurement. Another example of an equation for determining T1 is:

$$\Sigma_{pixels}(\text{red channel intensity value} + \text{pixels green channel intensity value})$$

The intensity value can be given by the camera on a standard 0-255 intensity scale.

T2 can be a subjective input measure of the user experience of "burning" sensation of the skin on a scale from 0 to 10. One or more embodiments of the present disclosure can include a user interface device such as a keyboard, keypad, or touch screen, for example, for the user to enter data. If no input is received, it is assumed that the burning sensation has a value of 0. Input may be made a keyboard or cell phone, for example. T3 is a subjective input measure of the user experience of "stinging" sensation of the skin on a scale from 0 to 10. If no input is received, it is assumed that the burning sensation has a value of 0. T4 is a measure of peeling: this may be determined by user input on a subjective scale of a rating from 1 through 10 or a severity rating may be obtained using a camera, a pictographic database of images labelled with severity of peeling and a deep learning algorithm, trained on the database of peeling image data, which classifies the severity of the peeling of the user via an image taken with the camera and fed to the deep learning classifier as input. In some cases, peeling may be considered as a therapeutic response, for example, in the case of exfoliation procedures.

"Therapeutic response" can be viewed as at least partially defining the second biological value during uses of the embodiment after the initial use. Measurements of therapeutic response depend on the disorder to be treated. Some examples are given below, however, it is understood that as sensor devices and measurement techniques improve, it may become practical to measure additional features of histological and clinical therapeutic response and adding or replacing those measurements listed below with new measurements to be tracked in a database and used to make dose adjustments at home based on data analysis concepts laid out here should be obvious to experts in the art or field.

For the anti-aging example worked here, therapeutic response measurements may be:

"R1"—a measure of Transepidermal Water Loss. A transepidermal water loss sensor, such as the Tewameter™ 300, by Courage-Khazaka Electronic GmbH, may be used.

"R2"—a measure of skin hydration. A corneometer, such as the CM 825 by Courage-Khazaka Electronic GmbH, may be used.

"R3"—a measure of wrinkle volume. This can be computed by the generation of facial topographies using 3D imaging techniques which include stereoscopic imaging, structured lighting techniques, laser range-finding or light angulation as described by in WO2014047712.

"R4"—a measure of collagen production. This can be estimated using the cumulative reduction in wrinkle volume, scars, or textural improvements of the face.

For users with acne:

"R1" can be a global severity rating found using deep learning methods and image database to classify the severity of the user's acne from his or her image captured using the camera device mentioned elsewhere in this patent.

"R2" can be the number of open comedones.

"R3" can be the number of closed comedones.

"R4" can be the number of pustules.

"R5" can be the number of nodules.

"R6" can be the number of cysts.

R2-R6 can be evaluated using image segmentation with a sliding window over the image, and by processing each segment with a trained machine learning classifier such as a deep convolution neural network or other architecture.

The response variable of greatest interest for determining dose in the case of acne can be the global severity assessment (R1).

For users with Psorasis:

"R1" can be a severity rating of the plaque psoriasis. This can be determined from photographs of the sufferers' psoriasis, user input regarding an estimate of the total percentage of skin covered by psoriasis or, in some embodiments, an assessment of total coverage may be based on total body imaging methodologies, and severity assessments may also be made using the methodology of deep leaning described above with an algorithm trained on a database of labelled severity photographs.

Other applications include treatments for Rosacea, Actinic Keratosis, sun damage and other ailments along with measures of the severity of the pathology similar to the above using either pictographic database of severity rating and deep learning, UV and IR imaging and sensing, images and image processing and related, appropriate, sensing methods to determine the therapeutic response variables.

For Actinic Keratosis, retinol dosing would be replaced by dosing of 5-Flourouracil, but the sensor based assessment of erythema and drug dosing algorithm would follow the same concept, beginning with concentrations between 5% and 0.5%, depending on skin sensitivity.

The presence of metabolites of the active ingredients delivered to the skin may also be measured. In this example, the active ingredient to be individually doses is retinoic acid, delivered in the form of a retinol microsponge solution.

Additional measurements can be taken by embodiments for deriving an initial value for the first biological property and for refining/revising the initial value. These measurements can include heart rate and stress level as measured using Galvanic skin response. These can be measured for example using the Empatica E4 wristband from Empatica Inc. This may be used, for example, for psoriasis sufferers to determine the extent to which stress predicts a breakout for a given sufferer by correlating increases of the skin response measured by the Empatica device and the severity of the psoriasis, as measured above. If a pattern of correlation between increased stress followed by increased psoriasis breakout severity is noted, for example, a notice may be sent to the user (for example via Bluetooth® or an internet connection to a cell phone) when predictive stress events occur and some topical treatment may be recommended in the appropriate dose for that user to be applied as a preventative measure.

The first biological property can also be at least partially based on data entered by a user. A standard questionnaire can be provided and the user can be classified as having one of four skin types (for example) based on answers to the questionnaire: (a) Sensitive skin, (b) Dry Skin, (c) Normal Skin, or (d) Oily Skin. Other classifications can be applied in one or more other embodiments of the present disclosure.

At 44, the computing device 10 can receive a second image input from the user 12. The second image input including a second image of the portion of the skin of the user 12 after application of the first formulation containing the first quantities of materials. The second image input can be in the same format as the first image input.

At 46, the computing device 10 can determine a second value of the second biological property of the user's skin based at least in part on the second image input. At 48, the computing device 10 can compare the first value of the second biological property and the second value of the second biological property. For example, the computing device 10 can determine if the skin of the user 12 evinces more or less irritation after the application of the first formulation.

At 50, the computing device 10 can change the first value of the first biological property of the user's skin to a second value of the first biological property of the user's skin based on the comparison. In other words, at least one baseline value applied in deriving a formulation can be changed in order to develop a subsequent formulation. This represents an application of feedback. The first value can be derived by applying an algorithm that includes at least one coefficient having a preliminary value. After the first formulation has been applied to the skin of the user 12 and the image of the skin after application has been processed, at least one coefficient of the algorithm can be changed from the preliminary value to a revised value. The first formulation can be based strictly on the first value of the first biological property of the skin of the user 12 but not based on the first value of the second biological property of the user's skin. In other words, the skin may not be irritated when the first formulation is derived. The second formulation can be derived based at least in part on the second value of the first biological property (the revised value) and also based at least in part on the second value of the second biological property of the user's skin (the level of irritation).

One or more implementations of the present disclosure can store formulations associated with a particular user and/or a particular skin sample, such as when a particular formulation used by a particular user and/or on skin having one or more particular attributes results in greater irritation, less irritation, or no change in a level of irritation. One or more implementations of the present disclosure can generate alerts or reports to a physician when a particular formulation used by a particular user and/or on skin having one or more particular attributes results in greater irritation, less irritation, or no change in a level of irritation. The reports can be configurable by the physician as desired.

At 52, the computing device 10 can determine a second formulation containing the plurality of materials based at least in part on the second value of the first biological property of the skin of the user 12. As set forth above, the second value of the first biological property can be different than the first value of the first biological property if the first formulation increased the level of irritation of the skin of the user 12. As with the first formulation, the computing device 10 can derive the second formulation based on data stored in memory 118.

At 54, the computing device 10 can control the plurality of servomotors 30, 130, 230 to dispense respective second quantities of the plurality of materials from at least some of the cavities 28, 128, 228. At least one of the second quantities of the plurality of materials is different than the corresponding quantity of the first quantities of the plurality of materials. In other words, the second formulation is different from the first formulation in terms of the materials used and/or the quantities of particular materials used. The second quantities are based on the second value of the first biological property of the skin of the user 12. It is noted that if the first formulation produced reduced irritation in the skin of the user 12, the computing device 10 can dispense the first formulation.

For sensitive skin and dry skin, as one example of the iterative, feedback process according to one or more embodiments of the present disclosure:

During days 0-14, the user can measure erythema using method T1 and also reports T2-T4, as well as inputting subjective data to an embodiment, such as satisfaction rating. Once this input is received, the embodiment can initialize a formulation including, by percentage, 0.01% of retinol, applied in the morning or evening. Standard concentrations of retinol available in the non-prescription market today are: minimal 0.01%, to 0.03%, 0.04% to 0.1% and stronger 0.5% to 1%.

Prior to the next dose (morning or evening), T1-T4 can be measured, as well as satisfaction. If user is not satisfied, then a note of the threshold irritation values recorded in T1-T4 is made and kept in memory as the user-subjective tolerance threshold values. If the user is not satisfied then the dose is reduced by 50%, if the user is very unsatisfied, then the dose is reduced to 0 for the next application. Once the dose is reduced, the measures T1-T4 are tracked until the user indicates that they are satisfied and the change in time of the measures T1-T4 are tracked.

If the user is satisfied, the dose is applied again after the measurements are taken up to a maximum of 2 days. If the user is still satisfied and the irritation threshold has not been surpassed, the dose is increased by 0.01% (or if the user was very sensitive initially, then the dose will be increased by an amount equal to the highest tolerated does (for example 0.005%)) until the threshold irritation level is indicated.

Once the threshold irritation level is indicated and the values of T1-T4 (with special attention to T1) are recorded, the dose of retinol can be decreased by 50% f the user is not satisfied and reduced to 0 if the user is very unsatisfied. The dose can then increased by 0.01% until value of T1 or T2-T4 are just below the threshold values. This value will now be called the maximum tolerated irritation value. The maximum tolerated irritation value is that value of T1-T4 measured at the dose level just below the dose level at which the user indicated the threshold level of irritation had been reached. Note that the required dose to reach the maximum tolerated irritation value need not be fixed and can change as the user acquires tolerance to the retinol treatment.

Once the maximum tolerated irritation value has been found, the retinol dose can be adjusted to the level that produced that value initially. The measurements T1-T4 will then be measured in the morning and at night (or just prior to applying the topical treatment) and the measurable change over time will be recorded. If the value of T1-T4 falls below the maximum tolerated value to the value of the second highest tolerated value recorded, the dose will be increased by 0.01%, such that the irritation level remains at the maximum tolerated irritation level.

Figure 4:
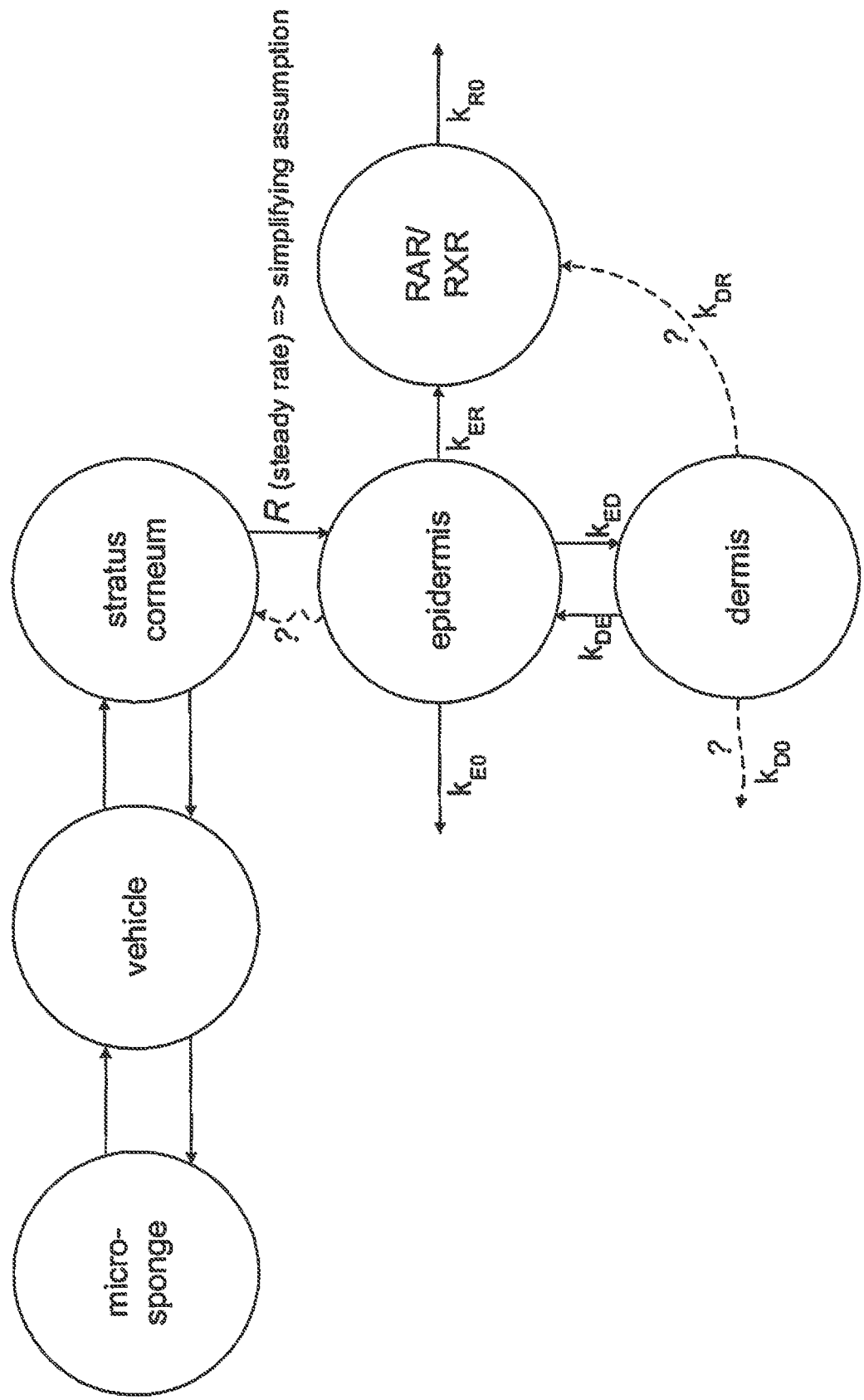
FIG. 4 is a simplified compartmental model.

During days 14-30, if necessary, the response variables can be recorded, along with the time and dose and stored in a database. In some embodiments this phase may be shortened. After day 14-30: Adapting standard models from Dermatokinetics (Murthy, 2011) and Pharmacokinetics (Rosenbaum, 2011), the simplified compartmental model shown in FIG. 4 is assumed for the distribution of retinoic acid (and its related forms (Vourhees, 2014)) made available from the retinol the skin.

Microsponge technology is a patented technology of Advanced Polymer Materials Inc. The following pharmacokinetic-pharmacodynamic model of response, or a very similar equation, is adapted from a general compartmental model (CARUSO, 2009) involving a central compartment (here taken as the epidermis) which receives a steady influx of drug dose (here modelled in R), an effect compartment and several compartments adjoining the central compartment (here only the dermis compartment adjoins the central compartment). Both the toxic variables and response variables are assumed to follow the sigmoidal response curve adapted from the above, however, in other embodiments and alternatives to this response curve, such as hermetic responses, may be developed and applied. In addition, moderate changes or development of these formulas may be obvious to those skilled in the art. The pharmacokinetic-pharmacodynamic model of response can be:

$$\text{Effect} = f(z) = \frac{E_{max} \times \left(k_{E0} \frac{z}{V1}\right)^{\gamma}}{\left(k_{E0} \frac{z}{V1}\right)^{\gamma} + (C50)^{\gamma}}$$

Where Effect may represent any one of T1, Ri and other continuous variables, and interpolations of discrete variables Ri, Ti and where:

$$z_{compliance} = R\left[\frac{A_E}{\alpha_E k_{R0}}(1 - e^{-k_{R0}t}) - \frac{A_E}{\alpha_E(k_{R0} - \alpha_E)}(e^{-\alpha_E t} - e^{-k_{R0}t}) + \frac{A_D}{\alpha_D k_{R0}}(1 - e^{-k_{R0}t}) - \frac{A_D}{\alpha_D(k_{R0} - \alpha_D)}(e^{-\alpha_D t} - e^{-k_{R0}t})\right]$$

It is approximated that R=r×dose. R is a rate of delivery of drug from stratus corneum to the epidermis via a controlled release microsponge/vehicle composition, which is approximated as a steady state rate proportional to the dose of retinol in the mixed product, with proportionality constant r.

Z is a consequence of the dermatokinetics of the retinoic acid (retinol derivative) in the skin and the parameters of Z are relevant for all possible measured effects, E. $A_E$ and $A_D$ are parameters representing the amount of retinoic acid in the "epidermis" and "dermis" compartments of the compartmental model, while $\alpha_E$ and $\alpha_D$ are theoretical parameters related to the time decay dynamics of the distribution of the retinol within the "epidermis" and "dermis" compartments. $k_{R0}$ is a parameter that describes the dynamics of the evacuation of retinoic acid from the retinoic acid receptor compartment (equivalent to the "effect" compartment in pharmacodynamics models) either through metabolism and/or excretion. These parameters, and the proportionality constant, will vary depending on the individual. "t" is the time over which a given dose is delivered, here it is set to 12 hours, the time frame between applications of product at a given dose and over which a steady injection of retinol will be delivered from the controlled release microsphere emulsion. However, this simplifying assumption may be relaxed in preferred embodiments. In this case the differential equations describing the system may be solved numerically, if necessary to make adjustments to the appropriate expressions for z in terms of R in order to improve performance. If we assume that the rate of metabolism and transfer of the drug between compartments is fast on the time scale of 12 hours over which the controlled release into the epidermis at rate R takes place. Thus:

$$z_{compliance} \cong r \times \text{dose} \times \left[\frac{A_E}{\alpha_E k_{R0}} + \frac{A_D}{\alpha_D k_{R0}}\right]$$

For non-compliance it is assumed that:

$$z_{non-compliance} \cong \left[\frac{A_E}{\alpha_E k_{R0}} + \frac{A_D}{\alpha_D k_{R0}}\right] \times \frac{e^{-k_{R0}t'}}{k_{ER}} + r \times \text{dose}_{last\ application} \times$$
$$\left[\frac{A_E}{\alpha_E(k_{R0} - \alpha_E)}(1 - e^{-\alpha_E T_{compliance}})(e^{-\alpha_E t'} - e^{-k_{R0}t'}) + + \right.$$
$$\left. \frac{A_D}{\alpha_D(k_{R0} - \alpha_D)}(1 - e^{-\alpha_D T_{compliance}})(e^{-\alpha_D t'} - e^{-k_{R0}t'})\right]$$

It follows that an adjustment parameter to z as a function of changing applied dose is derived from the time dynamics of z by solving the appropriate differential equations (CARUSO, 2009) to account for changes in the steady state rate of drug delivery, R, into the epidermis as the applied dose changes.

V1 is a parameter related to the theoretical volume of the "epidermis" compartment. This will vary from individual to individual. $T_{compliance}$ is the time over which the user was compliant with application and t' is the time since last compliance (product application).

The parameters V1 and those comprising the z quantity are the same for all measured effects, both toxic and therapeutic. $k_{E0}$ is a parameter representing the elimination rate of the retinoic acid (or related retinol and esters) from the "epidermis" compartment.

For each effect Ri and Ti the following parameters must be uniquely determined: the parameter γ is a measure of the sigmoldicity of the pharmacodynamics of the response to the retinoic acid dose resulting in the given effect, $E_{max}$ is the maximum pharmacodynamics response for a given effect and C50 is a parameter representing the concentration of drug in the "epidermis" compartment at which 50% of the maximum effect is achieved in theory.

C50 will change with time for toxic response as the user is desensitized to the toxic effects (Rosenbaum, 2011), specifically effects T1-T4. A model for C50 with the appropriate properties is:

$$C50 = \frac{C5\ Q_o}{1 + \left(\frac{C5\ Q_\infty}{C5\ Q_0} - 1\right)e^{-\frac{\tau}{T_{max}}}}$$

Where $C50_\infty$ represents the long term sensitivity of the user to the toxic effect after desensitization, $C50_\infty$ is the initial sensitivity and $T_{max}$ is a parameter related to the speed at which the user is desensitized to the toxic effect. The independent variable .tau. is the time the user has been applying the product diligently. A correction to C50 is applied for non-compliance such that τ is equal to the greater of the number of days of compliance minus the number of days of non-compliance or 0, or a measured model of non-compliance effects based on the user's measured irritation after non-compliance.

Thus there are 9 general pharmacokinetic parameters and 5 effect specific parameters that must be fit to the measured individual response as a function of dose. Given the first 14-30 days of data measurements from an individual user, these parameters may be fit using a standard mathematical software such as Mathematica.

Once these parameters have been found for an individual, the personalized dose is (when the assumption that the rate of metabolism and transfer of the drug between compartments is fast on the time scale of 12 hours over which the controlled release into the epidermis at rate R takes place:

$$\text{Dose}(\tau) = f^{1}(\text{Effect} = \text{maximum tolerated irritation}, \tau) / \left( r \left[ \frac{A_E}{\alpha_E k_{R0}} + \frac{A_D}{\alpha_D k_{R0}} \right] \right)$$

Where $$r \left[ \frac{A_E}{\alpha_E k_{R0}} + \frac{A_D}{\alpha_D k_{R0}} \right]$$

are found from fitting the measured effects, Effects=f(z), to the independent variable of the measured dose (from the mixer dispenser) and measured response data (as described in T1-T4, above) using the formulas for z_compliance and z_(non-compliance) as a function of dose as appropriate.

The materials retinol microsponge solution, oil and water vehicle and 15% L-ascorbic acid solutions and then combined in the mixer such that the concentration of the retinol microsponge solution is equal to Dose(τ).

Desired response effects will be reported to the user. This is expected to encourage compliance. As more data is collected from more users, the initial applied dose during days 0-14 will be adjusted to reflect the dose-response behavior of past users in the database that are identified to be similar to the user based on initial measurements.

It is noted that in other implementations, other forms of input can be directed to a computing device to derive formulations for application on the skin of the user 12. Electro-dermal measurement can be utilized, for example. Further, the user 12 can enter demographic data, such as scent preference or tint preference.

In one or more implementations of the present disclosure, data associated with the particular user 12 can utilized by a community of users. The data associated with the particular user 12 can be anonymized and stored in memory 118. Through the sharing of data and machine learning principles, one or more implementations of the present disclosure can increasingly define a reliable global severity rating scale using deep learning techniques by identifying latent variables detectable in images of skin. Further, such implementations can define facilitate telemedicine and automated dosing.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known procedures, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The term "and/or" includes any and all combinations of one or more of the associated listed items. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

The techniques described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

The present disclosure also relates to an apparatus for performing the operations herein. This apparatus may be specially constructed for the required purposes, or it may comprise a general-purpose computer selectively activated or reconfigured by a computer program stored on a computer readable medium that can be accessed by the computer. Such a computer program may be stored in a tangible computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and operations presented herein are not inherently related to any particular computer or other apparatus. Various general-purpose systems may also be used with programs in accordance with the teachings herein, or it may prove convenient to construct more specialized apparatuses to perform the required method steps. The required structure for a variety of these systems will be apparent to those of skill in the art, along with equivalent variations. In addition, the present disclosure is not described with reference to any particular programming language. It is appreciated that a variety of programming languages may be used to implement the teachings of the present disclosure as described herein, and any references to specific languages are provided for disclosure of enablement and best mode of the present invention.

The present disclosure is well suited to a wide variety of computer network systems over numerous topologies. Within this field, the configuration and management of large networks comprise storage devices and computers that are communicatively coupled to dissimilar computers and storage devices over a network, such as the Internet.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

While the present disclosure has been described with reference to an exemplary embodiment, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the appended claims. The right to claim elements and/or sub-combinations that are disclosed herein as other present disclosures in other patent documents is hereby unconditionally reserved.

We claim:

1. A computer-implemented method comprising:
   receiving, at a computing device having one or more processors, a first image input from a user, the first image input including a first image of a portion of the user's skin;
   determining, at the computing device, a first value of a first biological property of the user's skin and a first value of a second biological property of the user's skin, both first values based at least in part on the first image input, the first biological property representative of a sensitivity of the user's skin to one or more materials, the second biological property representative of a response of the user's skin to one or more materials;
   determining, at the computing device, a first formulation containing a plurality of materials, the first formulation based on the first value of the first biological property of the user's skin;
   receiving, at the computing device, a second image input from the user, the second image input including a second image of the portion of the user's skin after application of the first formulation containing the first quantities of materials;
   determining, at the computing device, a second value of the second biological property of the user's skin based at least in part on the second image input;
   comparing, at the computing device, respectively, the first value of the second biological property and the second value of the second biological property;
   updating, at the computing device, the first value of the first biological property of the user's skin to a second value of the first biological property of the user's skin based on said comparing; and
   determining, at the computing device, a second formulation containing the plurality of materials based at least in part on the second value of the first biological property of the user's skin.

2. The computer implemented method of claim 1 wherein the response is a therapeutic response of the user's skin to one or more materials.

3. The computer implemented method of claim 1 wherein the response is a toxic response.

4. The computer implemented method of claim 3 wherein the first formulation is configured to inhibit irritation of the user's skin based on the first value of the first biological property of the user's skin.

5. The computer implemented method of claim 4 wherein said determining the first value of the first biological property of the user's skin is further defined as:
   determining, at the computing device, the first value of the first biological property of the user's skin by applying an algorithm including at least one coefficient having a preliminary value.

6. The computer implemented method of claim 5 wherein said determining the second value of the first biological property of the user's skin is further defined as:
   updating, at the computing device, the at least one coefficient from the preliminary value to a revised value.

7. The computer implemented method of claim 4 wherein said determining the first formulation is further defined as:
   determining, at the computing device, the first formulation containing a plurality of materials based on the first value of the first biological property of the user's skin but not based on the first value of the second biological property of the user's skin.

8. The computer implemented method of claim 7 wherein said determining the second formulation is further defined as:
   determining, at the computing device, the second formulation containing the plurality of materials based at least in part on the second value of the first biological property of the user's skin and also based at least in part on the second value of the second biological property of the user's skin.

9. The computer implemented method of claim 4 wherein said determining the first value of the first biological property of the user's skin is further defined as:
   determining, at the computing device, the first value of the first biological property of the user's skin by, at least in part, counting a number of lesions in the first image.

10. The computer implemented method of claim 4 wherein said receiving the first image input is further defined as:
    receiving, at the computing device, the first image input from a user, the first image input including a first image of a portion of the user's skin and being an infrared image.

11. The computer implemented method of claim 4 wherein said receiving the first image input is further defined as:
receiving, at the computing device, the first image input from a user, the first image input including a first image of a portion of the user's skin and being an ultraviolet image.

12. The computer implemented method of claim 4 further comprising:
retrieving, by the computing device, data from a secondary memory physically remote from the computing device through a network during said determining the first formulation.

13. The computer implemented method of claim 12 wherein the data is associated with one of the user and others.

14. A computing device comprising:
one or more processors; and
a non-transitory, computer readable medium storing instructions that, when executed by the one or more processors, cause the computing device to perform operations comprising:
receiving a first image input from a user, the first image input including a first image of a portion of the user's skin;
determining a first value of a first biological property of the user's skin and a first value of a second biological property of the user's skin, both first values based at least in part on the first image input, the first value representative of a sensitivity of the user's skin to one or more materials, the second value representative of a response of the user's skin;
determining a first formulation containing a plurality of materials, the first formulation based on the first value of the first biological property of the user's skin;
receiving a second image input from the user, the second image input including a second image of the portion of the user's skin after application of the first formulation containing the first quantities of material;
determining a second value of the second biological property of the user's skin based at least in part on the second image input; comparing respectively, the first value of the second biological property and the second value of the second biological property;
updating the first value of the first biological property of the user's skin to a second value of the first biological property of the user's skin based on said comparing; and
determining a second formulation containing the plurality of materials based at least in part on the second value of the first biological property of the user's skin.

15. The computing device of claim 14 wherein the response is a therapeutic response of the user's skin to one or more materials.

16. The computing device of claim 14 wherein the response is a toxic response.

17. The computing device of claim 16 wherein the first formulation is configured to inhibit irritation of the user's skin based on the first value of the first biological property of the user's skin.

18. The computing device of claim 17 wherein the determining of the first value of the first biological property of the user's skin is further defined as determining the first value of the first biological property of the user's skin by applying an algorithm including at least one coefficient having a preliminary value.

19. The computing device of claim 18 wherein the determining of the second value of the first biological property of the user's skin is further defined as updating the at least one coefficient from the preliminary value to a revised value.

20. The computing device of claim 17 wherein the determining of the first formulation is further defined as determining the first formulation containing a plurality of materials based on the first value of the first biological property of the user's skin but not based on the first value of the second biological property of the user's skin.

21. The computing device of claim 20 wherein the determining of the second formulation is further defined as determining the second formulation containing the plurality of materials based at least in part on the second value of the first biological property of the user's skin and also based at least in part on the second value of the second biological property of the user's skin.

22. The computing device of claim 17 wherein the determining of the first value of the first biological property of the user's skin is further defined as determining the first value of the first biological property of the user's skin by, at least in part, counting a number of lesions in the first image.

23. The computing device of claim 17 wherein the receiving of the first image input is further defined as receiving the first image input from a user, the first image input including a first image of a portion of the user's skin and being an infrared image.

24. The computing device of claim 17 wherein the receiving of the first image input is further defined as receiving the first image input from a user, the first image input including a first image of a portion of the user's skin and being an ultraviolet image.

25. The computing device of claim 17 wherein said non-transitory, computer readable medium storing instructions further causes the computing device to perform an operation comprising:
retrieving data from a secondary memory physically remote from the computing device through a network during said determining the first formulation.

26. The computing device of claim 25 wherein the data is associated with one of the user and others.

27. A computer-implemented method comprising:
receiving, at a computing device having one or more processors, a first image input from a user, the first image input including a first image of a portion of the user's skin;
determining, at the computing device, a first value of a first biological property of the user's skin and a first value of a second biological property of the user's skin, both first values based at least in part on the first image input, the first biological property representative of a sensitivity of the user's skin to one or more materials, the second biological property representative of a response of the user's skin;
determining, at the computing device, a first formulation containing a plurality of materials, the first formulation based on the first value of the first biological property of the user's skin;
transmitting, at the computing device, the first formulation;
receiving, at the computing device, after said transmitting, a second image input from the user, the second image input including a second image of the portion of the user's skin after application of the first formulation containing the first quantities of materials;

determining, at the computing device, a second value of the second biological property of the user's skin based at least in part on the second image input;

comparing, at the computing device, respectively, the first value of the second biological property and the second value of the second biological property;

updating, at the computing device, the first value of the first biological property of the user's skin to a second value of the first biological property of the user's skin based on said comparing;

determining, at the computing device, a second formulation containing the plurality of materials based at least in part on the second value of the first biological property of the user's skin; and transmitting, at the computing device, the second formulation.

28. The computer implemented method of claim 1, wherein at least one of the first formulation and the second formulation is determined based at least in part on data received from at least one of a wearable sensor and a handheld sensor.

29. The computer implemented method of claim 28, wherein at least one of the wearable sensor and a handheld sensor includes a multi-photon optical sensor.

30. The computer implemented method of claim 1, wherein at least one of the first formulation and the second formulation is determined based at least in part on data stored in a database, wherein the database includes a cohort of users with similar features and projected dose response.

31. The computer implemented method of claim 30, wherein the data stored in the database includes demographic data, user satisfaction data or doctor-generated data.

32. The computer implemented method of claim 30, wherein at least one of the first formulation and the second formulation is determined based at least in part on application of machine learning principles to the data stored in the database.

33. The computer implemented method of claim 1, wherein the second formulation is further determined based at least in part on user satisfaction data.

34. The computer implemented method of claim 1, wherein the second formulation is further determined based at least in part on machine learning algorithms applied to at least one of the first image input and the second image input.

35. The computing device of claim 27 wherein the response is a therapeutic response of the user's skin to one or more materials.

36. The computing device of claim 27 wherein the response is a toxic response.

37. The computing device of claim 36 wherein the first formulation is configured to inhibit irritation of the user's skin based on the first value of the first biological property of the user's skin.

* * * * *